(12) United States Patent
Halm et al.

(10) Patent No.: US 6,485,492 B1
(45) Date of Patent: Nov. 26, 2002

(54) OSTEOSYNTHESIS DEVICE

(75) Inventors: Henry Halm, Bissendorf-Wissingen (DE); Bernd Schafer, Ennstrassa 27, CH-8316 Obaraqef (CH)

(73) Assignee: Bernd Schafer (CH)

(*) Notice: Subject to any disclaimer, the term of this patent is extended or adjusted under 35 U.S.C. 154(b) by 0 days.

(21) Appl. No.: 09/762,494

(22) PCT Filed: Jul. 10, 1999

(86) PCT No.: PCT/EP99/04853

§ 371 (c)(1),
(2), (4) Date: Feb. 7, 2001

(87) PCT Pub. No.: WO00/07511

PCT Pub. Date: Feb. 17, 2000

(30) Foreign Application Priority Data

Aug. 8, 1998 (DE) .......................... 198 35 816

(51) Int. Cl.⁷ .............................. A61B 17/70
(52) U.S. Cl. ........................... 606/61; 606/73
(58) Field of Search .............. 606/60, 61, 72, 606/73

(56) References Cited

U.S. PATENT DOCUMENTS

| 5,443,467 A | * | 8/1995 | Biedermann et al. ......... 606/65 |
|---|---|---|---|
| 5,486,174 A | | 1/1996 | Fournet-Fayard et al. .... 606/61 |
| 5,536,268 A | * | 7/1996 | Griss ............................. 606/61 |
| 5,624,442 A | | 4/1997 | Mellinger et al. ............. 606/61 |
| 5,669,911 A | * | 9/1997 | Errico et al. ................... 606/61 |
| 5,713,898 A | * | 2/1998 | Stucker et al. ................. 606/60 |
| 6,090,111 A | * | 7/2000 | Nichols ......................... 606/61 |

FOREIGN PATENT DOCUMENTS

| DE | 43 16 542 | 7/1994 |
|---|---|---|
| DE | 195 48 395 | 9/1997 |
| DE | 299 03 342 | 7/1999 |
| WO | WO 98 12976 | 4/1998 |

* cited by examiner

Primary Examiner—Nicholas D. Lucchesi
Assistant Examiner—Michael B. Priddy
(74) Attorney, Agent, or Firm—Young & Basile, PC

(57) ABSTRACT

An osteosynthesis device includes a bone screw and a correcting rod which is positioned and axially fixed in a fork head of the bone screw. To this end, the fork head includes means which prevent the longitudinal displacement of the correcting rod. In addition, the screw shank of the bone screw is mounted in the fork head such that it is able to move in relation to same and in the area in which it receives the screw shank said fork head is configured as a hollow cone.

20 Claims, 1 Drawing Sheet

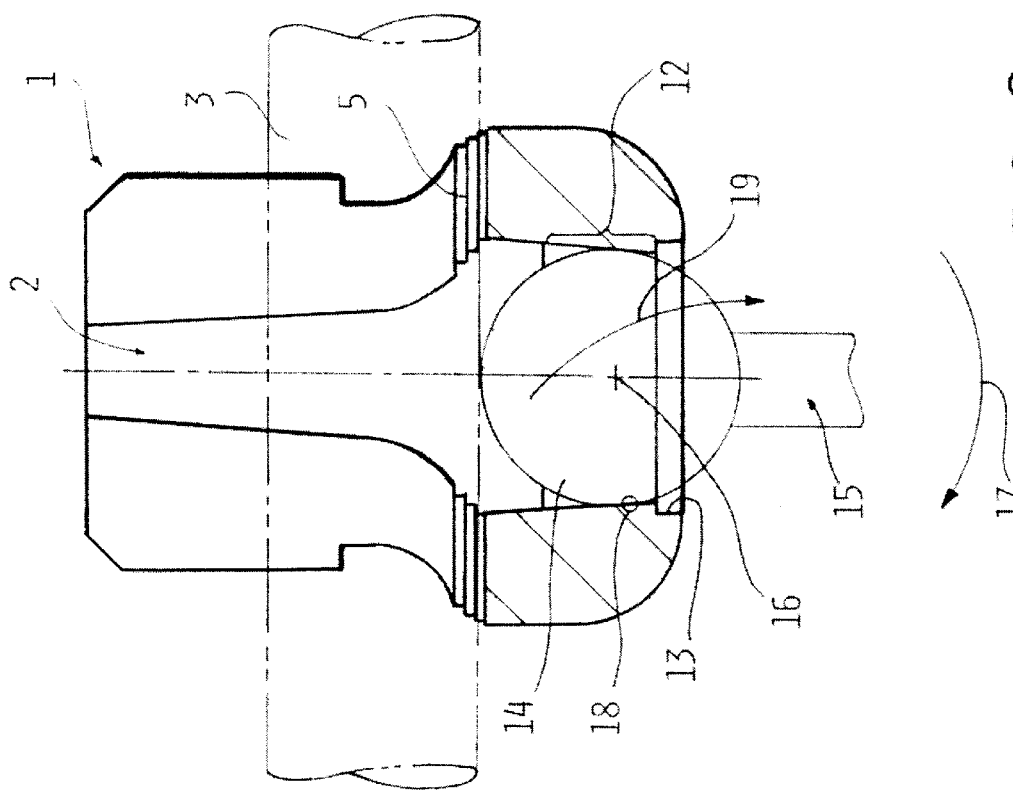
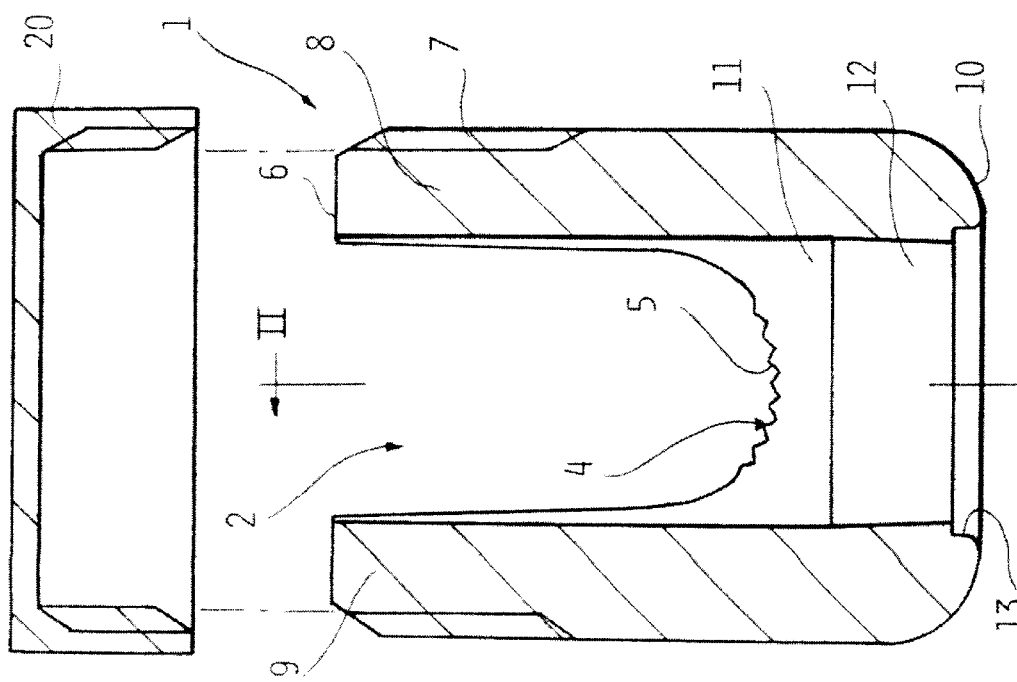

OSTEOSYNTHESIS DEVICE

BACKGROUND

The invention concerns an osteosynthesis device with a bone screw that has a screw shank head designed as a fork head, where the fork head has a groove running crosswise to the screw axis, and with a corrective rod, in which case the forked head is provided with a means for fixing the corrective rod, and the forked head has an axial opening and a spherical or partly spherical head of the screw shank is moveably inserted into the opening, in which case the opening becomes narrower in its region facing the screw shank and the narrowest cross section of the taper is larger than the diameter of the head of the screw shank.

A large number of osteosynthesis devices are known (DE-Gbm 90 04 240, DE-Gbm 91 04 027, EP-A-346 521, DE-A 39 42 429, EP-A-443 894, EP-A-348 272, EP-A-465 158, EP-A-528 706, EP-A-443 892, DE-A 39 16 198, DE-C 41 10 002, DE 43 16 542 C1). Various bone screws with forked heads are known from these publications, into which a corrective rod can be inserted and fixed. A nonslip anchoring of the corrective rod on the bone screw is thus basically obtained. Only a nonslip and nontwisting fixation of the corrective rod on the bone screw assures an optimal transfer of the tractional and compressive forces on the individual bones to be corrected and fixed as well as the transfer of torque and bending moments.

A good fixation is generally obtained by screwing a fixation screw into the forked bead so that it presses on the inserted corrective rod. However, it has turned out that a bending of the forked head due to the high forces and moments that occur is not precluded, such that the fixation of the corrective rod can loosen. In addition, such a clamping fixation does not offer sufficient security against a twisting of the corrective rod around its own axis.

A bone screw is known from U.S. Pat. Nos. 5,466,237, 5,474,555, 5,360,431 and 5,624,442. The bone screw has a forked head and a screw shank, where the head of the screw shank is supported swivellably in the forked head. An optimal orientation of the forked heads and thus the corrective rod can be obtained in this manner. This is achieved in that the screw shank had a partially spherical head that lies in a sort of ball socket that is provided in the forked head. The ball socket forms a spherical bearing for the head of the screw shank. It turned out, however, that particular care must be taken in the fixing and fastening of the screw shank on the forked head due to the multipart design of the bone screw. If loosening occurs here the goal of stabilizing and fixing the bone is not achieved. Under the circumstances, an immediate operation is necessary.

SUMMARY

The invention has as its basis the problem of further developing an osteosynthesis device of the above type so that loosening in the region of fixation of the screw shank on the forked head can be excluded.

This problem is solved according to the invention by designing the narrowing in the form of a truncated hollow cone.

In the osteosynthesis device designed according to the invention the forked head is not, as in the prior art, designed with a ball socket for accommodating the partially spherical head of the screw shank, but has a truncated hollow cone in the accommodation region of the head of the screw shank, in which the head of the screw shank is not merely lying (as is the case in the prior art) but is held clamped so that when the osteosynthesis device is tightened, the head of the screw shank is clamped in this truncated hollow cone profile so that it is fixed by the clamping. On the one hand, the manufacture of such a truncated hollow cone section is considerably simpler than the manufacture of a ball socket, which in any case has to be matched precisely to the diameter of the head of the screw shank. Even minute deviations here result in an unstable support of the screw head. On the other hand, an additional advantage is provided in that, by tightening the means fixing the corrective rod, the screw shank head is pressed into the truncated hollow cone-like narrowing so that it is deformed at least in the bearing region. In the prior art, the partial spherical head is merely pressed on the ball socket, whereby only a frictional closure is obtained. In the design according to the invention a positive locking is achieved besides the frictional closure.

It is provided in a further development that the hollow cone has a cone angle of 2–15°, in particular, 8°. A self-locking of the pressed-in screw shank head is achieved with such a cone angle so that even if the means fixing the corrective rod on the forked head is released and the corrective rod removed, the forked head is still securely fixed on the screw shank head.

It is provided in a further refinement that the center of the head of the screw shank lies inside the narrowing. This assures on the one hand that the head of the screw shank is held and pressed in the region of its maximum periphery so that the maximum moments are applied in the region of the pressing due to the maximum lever arm.

One embodiment provides that the opening, on its open end facing the screw shank, broadens by steps. Due to this stepped broadening, a greater clearance is obtained at the screw shank end of the forked head, by which the pivoting angle for the screw shank is enlarged.

To increase the stability of the forked head it is provided that the forked head has an accumulation of material in the region of the hollow cone-like opening. Due to the accumulation of material, plastic deformations of the forked head need hardly or at all be feared and failure due to cracks or the like is excluded. In particular, the accumulation of material is achieved by a great wall thickness. The wall thickness corresponds essentially to the wall thickness of the forked head in the region of the thread for the cap nut.

Additional advantages, features and details of the invention result from the following description, in which a particularly preferred embodiment example is presented in detail with reference to the drawing. The features shown in the drawing and stated in the specification can be actualized individually or in any combination in the invention.

BRIEF DESCRIPTION OF THE DRAWING

FIG. 1 shows a longitudinal section through the forked head according to the invention, and FIG. 2 shows a longitudinal section alone line II—II in FIG. 1 through the forked head with the inserted head of a screw shank.

DETAILED DESCRIPTION

The forked head 1 of an osteosynthesis device is shown in FIG. 1. This forked head 1 is provided with a groove 2, into which a corrective rod 3 (FIG. 2) is inserted. This corrective rod 3 is provided, for example, with longitudinal flutes, which engage in flutes 5 provided at the bottom 4 of groove 2. The forked head 1 is provided at the upper end 6 with an external thread 7, on which a means fixing the corrective rod 3 in the groove 2, e.g., a nut, in particular, a cap nut can be screwed. Not only is the corrective rod 3 pressed into the flutes 5 of the groove 2 with this cap nut, but the two sides 8 and 9 of the forked head 1 are also secured against expanding.

The groove 2 continues in the direction of the lower end 10 of the forked head 1 in a borehole 11 and a truncated hollow cone-like narrowing 12. The narrowing 12 is linear and has a cone angle of 8°. The narrowing 12 passes at the lower end 10 into a step-like broadening 13.

In FIG. 2, which shows the section II—II of FIG. 1, the head 14 of a screw shank 15 is inserted into the truncated hollow cone-like narrowing 12. The screw shank 15 is shown only schematically. It is readily detectable that the corrective rod 3 is seated both on the flutes 5 of the groove or channel 2 and also on the upper end of the head 14 and that when the cap nut (not shown) is drawn tight, the upper end of the head 14 and the adjacent region of the corrective rod 3 are deformed, in particular, plastically deformed. However, the head 14 is also pressed into the truncated hollow cone-like narrowing 12, in which case the narrowing 12 and the area of the head 14 in contact with it are also deformed here. In any case, the midpoint or the center 16 of the head 14 is inside of the narrowing 12.

If forces or moments arise on the screw shank 15 in the direction of the arrow 17, these moments effect a displacement of the head 14 around a swivel point 18 in the direction of the arrow 19, by which the head 14 is drawn further into the narrowing 12. This causes an increase in the pressing of the head 14 in the narrowing 12, by which the fixation and binding of the forked head 1 on the screw shank 15 are further increased.

It is also evident from FIG. 2 that the swiveling range of the screw shank 15 on the forked head 1 is increased by the broadening 13.

What is claimed is:

1. An osteosynthesis device with a bone screw that has a screw shank and a screw head in the form of a forked head, where the forked head has a groove running crosswise to the screw axis, and a corrective rod to be inserted into the groove of the forked head, where the forked head is provided with means for fixing the corrective rod, and the forked head has an axial opening and at least a partially spherical head of the screw shank is inserted moveably into the opening, the opening narrowing in its region facing the screw shank and the narrowest cross section of the narrowing is smaller than the diameter of the head of the screw shank, the corrective rod being seated on the upper end of the head of the screw shank, characterized in that the narrowing is in the form of a truncated hollow cone and the corrective rod deforms the head of the screw shank when the means fixing the corrective rod is drawn tight.

2. The osteosynthesis device according to claim 1, characterized in that a center of the head of the screw shank lies inside of the narrowing.

3. The osteosynthesis device according to claim 1, characterized in that the hollow cone has a cone angle of 2°–15°.

4. The osteosynthesis device according to claim 1, characterized in that the opening is broadened at an open end facing the screw shank.

5. A bone screw for an osteosynthesis device according to claim 1, in which the head of the screw shank projects over the bottom of the groove.

6. The osteosynthesis device according to claim 1 characterized in that the hollow cone has a cone angle of 8°.

7. The osteosynthesis device according to claim 1 characterized in that the opening is stepped broadened at an open end facing the screw shank.

8. The osteosynthesis device of claim 1 further comprising: at least one flute disposed at a bottom of the groove to engage the corrective rod.

9. The osteosynthesis device of claim 1 wherein the head of the screw shank is directly engageable with the opening along a circular periphery of the head of the screw shank.

10. The osteosynthesis device according to claim 1, characterized in that the forked head is provided with an increased wall thickness in the region of the hollow cone-like opening.

11. The osteosynthesis device according to claim 10, characterized in that the corrective rod has a surface profile the longitudinal direction and the forked head has a surface profiling in the bottom of the groove or channel.

12. An osteosynthesis device with a bone screw that has a screw shank and a screw head in the form of a forked head, where the forked head has a groove running crosswise to the screw axis, and a corrective rod to be inserted into the groove of the forked head, where the forked head is provided with means for fixing the corrective rod, and the forked head has an axial opening and at least a partially spherical head of the screw shank is inserted moveably into the opening, the opening narrowing in its region facing the screw shank and the narrowest cross section of the narrowing is smaller than the diameter of the head of the screw shank, the corrective rod being seated on the upper end of the head of the screw shank, characterized in that the narrowing is in the form of a truncated hollow cone and the corrective rod deforms the head of the screw shank when the means fixing the corrective rod is drawn tight and the head of the screw shank is directly engageable with the opening along a circular periphery of the head of the screw shank.

13. The osteosynthesis device of claim 12 wherein the opening further comprises:

a broadening portion adjacent the narrowest cross section; and a shoulder defined between the narrowest cross section and the broadening portion.

14. The osteosynthesis device of claim 12 further comprising:

a plurality of flutes disposed along a bottom of the groove wherein each flute extends longitudinally along the groove.

15. The osteosynthesis device of claim 12 wherein the opening defines a frusto-conical surface disposed at angle of eight degrees.

16. The osteosynthesis device of claim 12 wherein at least a portion of the head of the screw shank extends through the opening.

17. An osteosynthesis device with a bone screw that has a screw shank and a screw head in the form of a forked head, where the forked head has a groove running crosswise to the screw axis, and a corrective rod to be inserted into the groove of the forked head, where the forked head is provided with means for fixing the corrective rod, and the forked head has an axial opening and at least a partially spherical head of the screw shank is inserted moveably into the opening, the opening narrowing in its region facing the screw shank and the narrowest cross section of the narrowing is smaller than the diameter of the head of the screw shank, the opening also including a stepped broadened portion adjacent the narrowest cross section, the corrective rod being seated on the upper end of the head of the screw shank, characterized in that the narrowing is in the form of a truncated hollow cone and the corrective rod deforms the head of the screw shank when the means fixing the corrective rod is drawn tight and the head of the screw shank is directly engageable with the opening along a circular periphery of the head of the screw shank.

18. The osteosynthesis device of claim 17 further comprising:

a plurality of flutes disposed along a bottom of the groove wherein each flute extends longitudinally along the groove for engaging the connecting rod.

19. The osteosynthesis device of claim 18 characterized in that a center of the head of the screw shank is disposed in the opening.

20. The osteosynthesis device of claim 19 characterized in that the hollow cone has a cone angle of between two degrees and fifteen degrees.

* * * * *